United States Patent [19]

Ecanow et al.

[11] Patent Number: 4,547,490
[45] Date of Patent: Oct. 15, 1985

[54] SYNTHETIC WHOLE BLOOD AND A METHOD OF MAKING THE SAME

[75] Inventors: Charles S. Ecanow, Skokie; Bernard Ecanow, Wilmette, both of Ill.

[73] Assignee: Neomed, Inc., Wilmette, Ill.

[21] Appl. No.: 512,917

[22] Filed: Jul. 12, 1983

Related U.S. Application Data

[63] Continuation-in-part of Ser. No. 372,393, Apr. 27, 1982, abandoned.

[51] Int. Cl.$^4$ .................. A61K 37/00; A61K 31/685
[52] U.S. Cl. ...................................... 514/21; 514/76; 514/77; 514/78
[58] Field of Search .................. 424/177, 199; 514/21, 514/76, 77, 78

[56] References Cited

U.S. PATENT DOCUMENTS 2,591,133  4/1952  Campbell et al. .................. 260/117
4,001,401  4/1977  Bonsen et al. ...................... 424/177
4,002,739  1/1977  Turner et al. ....................... 424/177
4,133,874  1/1979  Miller et al. ........................... 424/38

FOREIGN PATENT DOCUMENTS 2940184  4/1981  Fed. Rep. of Germany .
742594  12/1955  United Kingdom .

OTHER PUBLICATIONS

Selkurt-Physiology-2nd Edit. (Little-Brown), (1966), p. 218.
Guyton-Basic Human Physiology (Saunders), (1971), p. 157.
Watanabe et al.–Chem. Abst., vol. 81 (1974), p. 16715v.
Campbell et al.–Chem. Abst., vol. 46 (1952), p. 6797a.
Ricketts–Chem. Abst., vol. 46 (1952), p. 1215f.
Kaplan et al.–Chem. Abst., vol. 83 (1975), p. 53540w.
Vinograd–Finkel et al.–Chem. Abst., vol. 77 (1972), p. 86318j.
Chem Abst.–8th Coll. Index, Benzimidazolin–By, pp. 5070, 5071, 5144 and 5145 (1972) and 5145s, 5146s and 5076s.
A. Veis and C. Aranyi, "Phase Separation in Polyelectrolyte Systems, I. Complex Coacervates of Gelatin", Journal of Physical Chemistry, vol. 64 (1960), pp. 203–210.
Merck Manual, 14th Ed., (Rahway, N.J.: Merck & Co., Inc., 1982).
Arthur Osol, Ed., *Remington's Pharmaceutical Sciences* (Easton, Pa.: Mack Publishing Co., 1975), p. 315.
J. McMullen et al., "Pectin–Gelatin Complex Coacervates", Journal of Pharmaceutical Science, vol. 71, No. 6 (Jun., 1982), pp. 628–633.
H. H. deJong in *Colloid Science* by H. R. Kruyt, vol. ii (Elsevoir, Amsterdam, 1949).
Gessner G. Hawley, Ed., The Condensed Chemical Dictionary, 9th Ed., (New York: Van Nostrand Reinhold Company, 1977), p. 213.
"Blood", *Van Nostrand's Scientific Encyclopedia*, 1968, pp. 214–215.
Documenta Geigy, (Basle, Switzerland: J. R. Geigy, 1956).
*Geigy Scientific Tables*, 8th Ed. (Basle, Switzerland: Ciba-Geigy, Ltd., 1982).
Department of Defense, Document No. 84-R-0033, p. 7.
Ostra, *Liposomes*, (New York: Marcelle–Deeker, 1980).
R. Goodman et al., "Cytotoxicity of a Perfluorocarbon Blood Substitute to Macrophages in Vitro", Science, vol. 220, (May, 1983), pp. 965–967.
P. Lundsgaard–Hansen, M.D. and B. Tschirren, M.D., "Modified Fluid Gelatin as a Plasma Substitute", *Blood Substitutes and Plasma Expanders*, (New York: Alan R. Liss, 1978), p. 227.
Merck Manual, 10 Ed. (Rahway, N.J.: Merck & Co., Inc., 1983).
Ashwood–Smith, M. S., "Polyvinyl–Pyrolidone Solutions Used in Plasma Expander Potential Carcinogens"; Lancet 1 (1971), p. 1304.
Towers, R. P., "Lymph Node Changes Due to Polyvinyl–Pyrolidone"; Journal of Clinical Pathology 10, (1975–1977), p. 1957.
DeVenute, Frank and Zegna, Angelo, "Blood Exchanger with Pyridoxilated and Polymerized Hemoglobin Solution", *Surgery, Gynecology and Obstetrics*, vol. 155, (Sep., 1982), pp. 342–346.

Primary Examiner—Sam Rosen
Attorney, Agent, or Firm—Ladas & Parry

[57] ABSTRACT

A composition of matter which comprises a synthetic whole blood useful as a substitute for whole natural blood and a method of making the same are disclosed. The method of manufacture yields a composition of matter comprised of a two phase coacervate system. The claimed system successfully duplicates the two phase heterogeneous physicochemical system of naturally occurring whole blood. Also, disclosed is a phase of the claimed method of manufacture which produces a composition of matter, useful as a substitute for hematocrit. Also disclosed is an embodiment employing a hemoglobin component selected from stroma free hemoglobin, synthetic liposomes containing stroma free hemoglobin, microencapsulated stroma free hemoglobin, microspheres of albumin containing stroma free hemoglobin, or emulsified droplets of the coacervate phase containing stroma free hemoglobin. It is preferred that the size of the hemoglobin component particles and the globules of the synthetic hematocrit and the synthetic whole blood range in size from 0.1 to 10 microns.

19 Claims, No Drawings

SYNTHETIC WHOLE BLOOD AND A METHOD OF MAKING THE SAME

This is a continuation-in-part of our copending U.S. Ser. No. 372,393, filed Apr. 27, 1982 now abandoned.

BACKGROUND

With the exception of applicant's U.S. Pat. No. 4,343,797, authorities in medicine and surgery are agreed that no acceptable substitute for whole human blood now exists. Similar opinion is widespread regarding a substitute for naturally occurring hematocrit.

Compositions such as Albumin, Lactated Ringer's Solution, Dextran, Modified Gelatin, Hydroethyl Starch, Fluorocarbons, and Perfulorocarbons are known in the literature as "Blood Substitutes". (Reference: Chemical Abstracts, 8th Collective Index, 1967–1971). The use of these compositions is restricted to the transport of oxygen and carbon dioxide and the expansion of plasma volume. There is no recorded evidence that these compounds can function as *whole* blood substitutes or that they are ever used as such. (Reference: Chemical Abstracts; volumes 88, 89, 90, 91, 92, 93 and 94; Index Medicus; annual volumes 1967 to 1981; monthly volumes: January, February, March 1982) Further, the scientific literature cited above records the fact that the use of the aforementioned "blood substitutes" is restricted not only because of their physiological limitations but also because of the adverse reactions and incompatibilities associated with their use.

TABLE I

| Properties* | Whole Human Blood | U.S. Pat. No. 4,343,797 Synthetic Whole Blood | Present Invention Synthetic Whole Blood Albumin |
|---|---|---|---|
| 1 | Yes | Yes | Yes |
| 2 | Yes | Yes | Yes |
| 3 | Yes | Yes | Yes |
| 4 | Yes | Yes | Yes |
| 5 | Yes | Yes | Yes |
| 6 | Yes, but not equal to that of synthetic whole blood | Yes | Yes |
| 7 | No | Yes | Yes |
| 8 | Yes | Yes | Yes |
| 9 | Increase | Can be prepared to decrease or increase % | Can be prepared to decrease or increase % |
| 10 | Yes | Yes | Yes |
| 11 | Yes | No | No |
| 12 | No | Yes | Yes |
| 13 | No | Yes | Yes |

| Properties* | Lactate Ringer's Solution | Dextran | Gelatin including modified gelatin | Albumin 5% | Hydroethyl Starch | Perfluoro chemicals |
|---|---|---|---|---|---|---|
| 1 | No | No | No | No | No | Yes |
| 2 | Yes | Yes | Yes | Yes | Yes | Yes |
| 3 | No | No | No | No | No | No |
| 4 | No | No | No | No | No | No |
| 5 | No | No | No | No | No | Yes |
| 6 | No | No | No | No | No | No |
| 7 | No | No | No | No | No | No |
| 8 | No | No | No | No | No | No |
| 9 | Reduction | Reduction | Reduction | Reduction | Reduction | Reduction |
| 10 | Yes | Yes | Yes | Yes | Yes | Yes |
| 11 | Does Not | Does Not | Does Not | Does Not | Does Not | Yes |
| 12 | No | No | No | No | No | Yes |
| 13 | Yes | Yes | Yes | Yes | Yes | Yes |

Properties*
1 Oxygen Transport
2 Carbon Dioxide Transfer
3 Oxygen can be held in reserve and released in accordance with physiological tension
4 Hemoglobin can be added or dispersed within the preparation without loss of stability
5 Transfers gasses other than $O_2$ and $CO_2$
6 Possesses both polar and non-polar properties
7 Dissolves and transports nonpolar drug entities without loss of dosage-form stability
8 Transports enzyme systems without loss of stability
9 Effect on hematocrit percent after transfusion
10 Essential amino acids can be transported in stable form and desired quantity
11 Oxygen uptake ability reduced at low $O_2$ partial pressures
12 Transports physiologically useful lipid soluble entities as a stable solution
13 Universal donor characteristics Table I compares (1) the presently disclosed invention with (2) synthetic whole blood (U.S. Pat. No. 4,343,797, (3) whole human blood and (4) the known available substitutes. Note should be taken of the striking functional similarities between the presently disclosed invention, the composition of U.S. Pat. No. 4,343,797 and whole human blood.

THE PHYSICO-CHEMICAL STRUCTURE OF WHOLE HUMAN BLOOD

From a physico-chemical point of view, whole human blood in the body exists and the functions as a two phase coacervate system. Erythrocytes, largely composed of water, comprise the relatively non polar coacervate phase of the coacervate system referred to above. Plasma consisting primarily of water constitutes the bulk water, relatively polar aqueous phase of the coacervate system. Normally, the two phases exist in equilibrium with respect to dissolved molecules and electrolytes.

The claimed invention successfully substantially duplicates the two phase physico-chemical system of whole human blood. As such, the claimed composition can carry out virtually the entire range of physiological functions of whole human blood, with the exception of clotting. Infusion of the claimed synthetic whole blood however, will not interfere with the clotting ability of the recipient's blood. Analysis of the presently known "blood substitutes" indicates that none of them are comprised of the two phase coacervate system of the disclosed invention.

OBJECTS

It is an object of this invention to provide an acceptable substitute for whole mammalian blood. It is another object to provide a convenient method for preparing an acceptable substitute for whole mammalian blood. It is a further object to provide a useful substitute for naturally occurring hematocrit and to provide a convenient method for preparing the hematocrit substitute. Further object will become evident from the details of the disclosure.

PRIOR METHOD AND COMPOSITION

In order to understand fully the improvement over the prior method and composition, disclosed in this application, it is necessary to review as background the Applicants' U.S. Pat. No. 4,343,797 issued Aug. 10, 1982 incorporated herein by reference. That invention comprises a composition of matter useful as a safe and effective substitute for whole natural mammalian blood and a method for the manufacture thereof. The disclosed invention incorporates components which are endogenous to whole human blood. They are combined in such manner as to yield a two phase coacervate system substantially identical to the two phase coacervate system identical to the two phase coacervate system of whole human blood. In the claimed method of manufacture, the coacervate phase of the two phase system can comprise from 1.0% to 99% of the system. The bulk water equilibrium phase can constitute from 99% to 1.0% of the coacervate system.

The coacervate phase substantially possesses the physiological and physico-chemical properties of naturally occurring hematocrit. The bulk water equilibrium phase of the system is substantially the physiological and physico-chemical equivalent of naturally occurring blood plasma. Upon emulsification, the two phase coacervate system can be infused into a recipient and will function as whole, natural blood. In the preferred method, the two phase coacervate system is brought into even closer functional equivalence with whole natural blood by the additon of appropriate proteins, electrolytes, a sterol, and if desired, a hemoglobin component before the system is emulsified. It is highly preferred, but not required, that the hemoglobin component is selected from stroma free hemoglobin, synthetic liposomes containing stroma free hemoglobin, microencapsulated stroma free hemoglobin, microspheres of albumin containing stroma free hemoglobin, or emulsified droplets made of the coacervate phase and containing stroma free hemoglobin. Other hemoglobin components may be employed. Sufficient hemoglobin component is added so that the final product contains about 1-20% weight to volume of stroma free hemoglobin.

When preparation of the two phase coacervate system is completed, the two phases may be separated by any of the conventional methods. In the preferred separation procedure, the two phases are separated after the ingredients described immediately above have been added to the coacervate system and mixed vigorously.

Upon separation of the two phases, the coacervate phase can be safely introduced intravenously and will carry out or enhance substantially all of the physiological functions of natural hematocrit. It can transport and transfer oxygen much as naturally occurring erythrocytes do. When introduced into the circulation, the disclosed hematocrit substitute (i.e. the coacervate phase of the two phase coacervate system) will not adversely affect the hematocrit percent of the recipient's hematocrit. On infusion, said hematocrit substitute will disperse in the blood plasma of the recipient, thereby contributing to the two phase coacervate system of the recipient's blood. In addition, the physicochemical characteristics of the claimed hematocrit substitute render it sensitive to the oxygen tensions of the tissues. Its rate of oxygen release is determined accordingly. Finally, the claimed hematocrit substitute can readily enter and pass through the major blood vessels, capillaries and the microcirculation.

If the intended purpose is to transfuse the equivalent of whole natural blood, then one of the emulsified forms of the two phase coacervate system is used. In the preferred method, the emulsified form of the coacervate system containing the previously described additives is transfused. The claimed compositions will, on introduction into the circulation, carry out virtually all of the vital functions of naturally occurring whole blood. It can establish, re-establish and/or maintain normal osmotic pressures, transport and transfer physiological gases, carry nutrients, drug dosage forms and various other useful physiological entities over extended periods of time without loss of stability. The transport characteristics of the disclosed composition make it an ideal vehicle for hyperalimentation procedures. In addition, it can be safely used in the establishment and maintainance of extra corporeal circulation. When it is desireable to introduce enzymes or enzyme systems into the body, such enzymes can be added to the claimed invention prior to emulsification. When infused through the synthetic whole blood, enzymes and enzyme systems will perform their normal physiological functions.

The intrinsic oxygen transport capacity of the disclosed composition can be enhanced by the addition of a hemoglobin component selected from stroma free hemoglobin, synthetic liposomes containing stroma free hemoglobin, microencapsulated stroma free hemoglobin, microspheres of albumin containing stroma free hemoglobin, or emulsified droplets containing stroma free hemoglobin, to the separated coacervate phase or alternatively, to the coacervate system, prior to emulsification. Addition of this substance does not affect the stability or the physiological capability of the claimed composition(s).

The disclosed synthetic whole blood is free of foreign proteins and other elements which contribute to the adverse reactions associated with the transfusion of whole human blood. Further, this invention possesses universal donor characteristics. Accordingly, blood typing is unnecessary prior to transfusion of the claimed compositions.

The disclosed synthetic whole blood and the hematocrit substitute can be used immediately after manufacture or stored for extended periods if refrigerated from 4 to 10° C. without loss of stability or utility.

The guidelines govern the quantities of synthetic whole blood that may be safely infused are substantially identical to those which govern the use of whole human blood. On infusion, the claimed compositions will circulate readily throughout the entire vascular system including the microcirculation.

Certain treatment procedures may make the addition of mucopolysaccharides, glycoproteins, proteins or other molecules, such as heparin, etc. desireable. These substances can be added to the synthetic whole blood at the appropriate point of manufacture. On infusion of the composition, these substances will carry out their usual function without affecting the stability or other properties of the claimed synthetic whole blood.

SUMMARY OF THE INVENTION

This invention constitutes a significant advance over the composition(s) and method disclosed in U.S. Pat. No. 4,343,797, issued on Aug. 10, 1982 mentioned above. This advance is based upon the inventor's discovery that incorporating a non-polar solvent as an additional ingredient in the method of preparing the compositions disclosed in the aforementioned patent application produces compositions with unique solvent properties. Further, compared to the compositions described in the prior application, the presently claimed compositions of matter are (1) more stable; (2) more non polar and (3) can transport larger quantities of oxygen and carbon dioxide. In addition, the use of an appropriate non ionic surfactant as employed in this invention, hastens the process of coacervation.

Any of a number of non polar solvents may be used to achieve the results described above. The following groups contain compounds useful for this purpose; the alcohols; (example: butanol) the esters; (example: ethyl acetate) the ketones; (example: dibutanol ketones) substituted glycerols; (examples: glycerol mono-acetate, glycerol di-acetate, glycerol tri-acetate) and the substituted hydrocarbons; (example: di-chloromethylene). In this invention, the preferred ingredient is glycerol dioleate.

This invention comprises a composition of matter useful as a safe and effective substitute for whole, natural blood and methods of manufacture thereof. The claimed invention makes use of the concepts and process of coacervation and incorporates components which are intrinsic to whole blood. In the process of manufacture the component ingredients may be either natural or synthetic in origin. The claimed process of manufacture produces a two phase coacervate system substantially identical to the two phase physicochemical system of whole natural blood, i.e.: a non-polar coacervate phase insoluble in *and* in equilibrium with an associate polar bulk water equilibrium phase.

The present invention also contemplates that in the preferred method, however, the two phase coacervate system is brought into even closer functional equivalence with whole, natural blood during the process of manufacture, by the addition of appropriate proteins, electrolytes, a sterol, and if desired, a hemoglobin component. The hemoglobin component is preferably selected from stroma free hemoglobin, synthetic liposomes containing stroma free hemoglobin, microencapsulated hemoglobin, microspheres of albumin containing stroma free hemoglobin, or emulsified droplets made of the coacervate phase containing stroma free hemoglobin.

As it now appears in the literature, the stroma free hemoglobin contained in the synthetic liposomes are considered to be synthetic erythrocytes. (Reference: Miller, I. and Djordjevich, L.; U.S. Pat. No. 4,133,874 (1979). With regard to the Miller and Djordjevich reference, the possibility is mentioned that the synthetic liposomal erythrocytes that they have invented can be suspended in isotonic saline or Krebs-Ringer solution or in synthetic plasma materials and used for blood transfusion purposes. Since the vehicles given above contain large quantities of bulk water, there is a strong likelihood that oxygen uptake in such compositions is limited. This stands in direct contrast with the oxygen uptake capability of the presently disclosed invention when the hemoglobin components in the form of microencapsulated hemoglobin and/or synthetic liposomes containing stroma free hemoglobin is incorporated in the claimed coacervate system or the coacervate phase of such a system. Both the claimed coacervate system and the claimed coacervate phase of the system have significant oxygen pick up. The addition of stroma free hemoglobin in other of the forms given immediately above serves significantly to enhance the oxygen uptake of these claimed compositions.

At the point that manufacture of the two phase coacervate system is completed, the two phases may be separated. In the preferred procedure, the two component phases are separated after the additives described above have been added but before emulsification takes place.

DETAILED DESCRIPTION

The manufacture of the claimed compositions must be carried out under aseptic conditions. Except for those steps involving refrigeration, all other procedures are performed at ambient temperatures. If it is desired, the compositions may be stored from 4° to 10° C. Wheninfused into humans, the compositions should be at a temperature that approximates normal body temperature.

The following is a description of the preferred method of preparing the claimed compositions. Specific examples of the practice of this invention are detailed in the following sections of this application.

The claimed compositions are prepared in the following manner:

Disperse from 5 to 25% weight to volume of powdered albumin in distilled water containing 0.9% weight to volume of a salt, preferably NaCl, 1 to 5% weight to volume urea and 0.1 to 10% weight to volume of lecithin. To this solution, add glycerol dioleate dropwise until globules of the coacervate phase appear. At this point, the solution is stored, undisturbed at 4° C. for 12 hours. At the end of this period of storage, a two phase coacervate system will have formed. The next step consists of adding such amount of distilled water at ambient temperature as will result in 5 to 25% weight to volume of albumin. Such quantity of a salt, preferably NaCl is then added to the coacervate system as will render said system isotonic with whole human blood. At this point, there two manufacturing options: the coacervate system can be separated into its two component phases, or alternatively, the system can be emulsified to produce droplets ranging in size from 0.1 to 10 microns. If the phases are separated, the coacervate phase can be used as a hematocrit substitute. If the system is emulsified, the composition can be used as a whole mammalian blood substitute. Storage should be from 4° to 10° C.

In the preferred method of manufacture, emulsification of the two phase coacervate system is delayed until the procedures described immediately below are completed.

Add such amount of cholesterol as will result in a 0.1 to 2% weight to volume concentration of cholesterol in said coacervate system. Next, add calcium chloride to a concentration of 1 to 5 mg% and potassium chloride to a concentration of 1 to 3 mg%. The preparation is then titrated using sodium bicarbonate until a pH in the range of 7.0 to 7.6, and preferably 7.3 to 7.45 is reached. On completion of the titration step, add such quantity of distilled $H_2O$ as will render the two phase coacervate system isotonic with whole human blood. The preparation is now mixed vigorously for 1 hour, and then stored at 10° C. for from 24 to 148 hours. Longer periods of storage will yield greater quantities of the coacervate phase. At the end of the storage period, the preparation is then allowed to reach room temperature. Next, the product is emulsified to produce droplets ranging in size from 0.1 to 10 microns. The composition that results from these procedures constitutes the basis of the claimed synthetic whole blood. Storage, if necessary should be at from 4° to 10° C.

If it is desired, the two phases of the coacervate system described immediately above may be separated prior to the emulsifyng step. If the phases are separated, the separated coacervate phase is useful as a hematocrit substitute. A hemoglobin component selected from stroma free hemoglobin, synthetic liposomes containing stroma free hemoglobin, microencapsulated stroma free hemoglobin, microspheres of albumin containing stroma free hemoglobin, or emulsified droplets made with the coacervate phase and containing stroma free hemoglobin, can be added as an option, to the coacervate system. If this election is made the quantities of the hemoglobin component added should be such that the final product contains 1-20% weight to volume of stroma free hemoglobin. The addition of a form of stroma free hemoglobin to either the coacervate phase or the coacervate system will enhance the intrinsic oxygen transport capacity of either of the claimed compositions of matter.

The procedures described above indicate that a phospholipid is a desired component in this invention. Lecithin is the preferred phospholipid in preparing the disclosed compositions of matter. However, any of the following or mixtures thereof can be used in place of lecithin: isolecithin, sphingomyelin, phosphatidyl serine, phosphatidyl inositol, phosphatidyl choline and phosphatidic acid. Other suitable compounds of the phospholipid group can be used.

Cholesterol is the preferred sterol in the manufacture of the claimed compositions. However, any of the following sterols can be used in place of the preferred cholesterol: ergosterol, 7 dehydrocholesterol, $\alpha$ sitosterol, $\beta$ sitosterol, $\gamma$ sitosterol, campesterol or mixtures thereof. Other compounds of this group known to those skilled in the art may also be used.

Reference has previously been made to the compounds that may be used in place of the preferred glycerol dioleate in the manufacture of the claimed compositions.

While the description given above contain many specificities, these should not be construed as limitations on the scope of the invention but rather as examplifications of preferred embodiments.

SPECIFIC EXAMPLES

Examples of the methods which may be used to manufacture the claimed compositions of matter follow:

EXAMPLE 1

25 grams of albumin are added to 500 mls of distilled water containing 0.9% weight to volume of sodium chloride, 3% weight to volume of urea and 500 mls of a 2½% solution of lecithin. Glycerol dioleate is added dropwise to the solution until globules of coacervate appear. The solution is then stored at 4° C. for 12 hours. At the end of this period, the solution is removed from storage and permitted to reach room temperature, after which 1 gram of cholesterol, 0.2 gram of calcium chloride and 0.4 gram of potassium chloride are added. The pH of the solution is adjusted to 7.35 by adding the necessary amount of sodium bicarbonate. The coacervate system is then made isotonic with whole human blood by addition of the required amounts of sodium chloride and distilled water. Following this step, the solution is mixed vigorously for 1 hour. It is then stored at a temperature of 10° C. for 72 hours. At the end of this period of storage, the solution will have separated into two distinct layers. The lower layer comprises the coacervate phase of the two phase coacervate system; the upper layer comprises the equilibrium bulk water phase of said system.

The two phases of the coacervate system can be separated or emulsified for the purposes and in the manner described previously in this disclosure. Storage of the products derived from this method should be 4° to 10° C.

EXAMPLE 2

200 mls of a 2½% lecithin solution are added to 200 mls of a 4% solution of albumin. 0.9% weight to volume of sodium chloride and 1.0 gram of urea are then added to the above solution. Glycerol diprionate is then added dropwise until globules of coacervate begin to appear. The remainder of the procedure follows Example 1.

EXAMPLE 3

200 mls of a 4% isolecithin solution are added to 200 mls of a 5% albumin solution containing 0.9 weight to volume of sodium chloride and 1% weight to volume of urea. Glycerol mono acetate is added dropwise to the above solution until droplets of coacervate begin to appear. The remainder of the procedure follows Example 1.

EXAMPLE 4

500 mls of 2½% lecithin solution are added to 500 mls of a 5% stock solution of human albumin. To this solution, 9 grams of sodium chloride, 9 grams of urea and 0.1 gram of ergosterol are added. Butanol is then added dropwise until globules of coacervate begin to appear. The remainder of the procedure follows Example 1.

EXAMPLE 5

500 mls of 2½% solution of isolecithin are added to 500 mls of a 5% stock solution of human albumin. To this mixture, add 5 grams of sodium chloride, 9 grams of urea and 0.1 gram of ergosterol. Ethyl ether is then added dropwise until globules of coacervate appear. The solution is then stored at 4° C. for 12 hours. After this period of storage, add such amount of distilled water as will result in a 5% weight to volume of albumin. Next, add such amount of sodium chloride as will render the solution isotonic with whole human blood. Follow this step by emulsifying the solution to produce droplets which range in size from 0.1 to 10 microns.

EXAMPLE 6

This procedure follows Example 1 with the following exceptions: (a) di-chloromethylene is added dropwise to the solution containing albumin, distilled water, sodium chloride, urea and lecithin, in place of glycerol dioloeate and (b) prior to the emulsification step, 50 grams of stroma free hemoglobin are added and thoroughly swirled to achieve a uniform dispension throughout the coacervate system.

EXAMPLE 7

The procedure of Example 6 is followed except that in (b) microencapsulated stroma free hemoglobin is added instead of stroma free hemoglobin.

EXAMPLE 8

The procedure of Example 6 is followed except that in (b) microspheres of albumin containing stroma free hemoglobin is added instead of stroma free hemoglobin.

EXAMPLE 9

The procedure of Example 6 is followed except that in (b) synthetic liposomes containing stroma free hemoglobin is added instead of stroma free hemoglobin.

EXAMPLE 10

The procedure of Example 6 is followed except that in (b) emulsified droplets made with the coacervate phase and containing stroma free hemoglobin is added instead of stroma free hemoglobin.

EXAMPLE 11

This is the procedure with regard to the above Examples to prepare and to employ microencapsulated stroma free hemoglobin. It occurs *after* the coacervate system has been formed, the phases are separated, and 2 to 5% of a stroma free hemoglobin component has been added to the lower coacervate layer. The lower coacervate layer containing the stroma free hemoglobin is combined with the equilibrium liquid water layer and emulsified so that the final emulsion contains particles (droplets) which can range from 0.1 to 10 microns in size. Next, 1 to 5% formaldehyde solution is added dropwise to the emulsified preparation until the desired degree of shell structuring of the droplets is achieved. The degree of structuring can range from semi-solid or gel-like to rigid, and is achieved either through the amount of formaldehyde added or through the length of the period of storage. After the desired degree of structuring is achieved, the preparation is stored anywhere between 5 to 40 hours at 20° to 40° C. On removal from storage, the preparation will have separated into two layers, the bottom one of which contains microencapsulated globules substantially spherical in shape, containing stroma free hemoglobin. The upper layer consists of equilibrium liquid water. The two layers are separated by means of a separatory funnel or other acceptable means. The microencapsulated spheres are washed with the equilibrium liquid water, until substantially all traces of fomaldehyde are completely removed. The microencapsulated spheres containing stroma free hemoglobin can then be dispersed in physiological saline solution, in the coacervate phase of any of the herein described coacervate systems, or added to the coacervate phase of the two phase coacervate system. After this step, the composition is them emulsified. The resultant emulsion is prepared so that the droplets can range in size from 0.1 to 10 microns. When the microencapsulated spheres containing stroma free hemoglobin are incorporated into the two phase coacervate system as described above, the result of the procedure is microencapsulated globules containing stroma free hemoglobin incorporated in droplets of the coacervate phase which in turn is suspended in the equilibrium liquid water phase.

In practice, where optimal sustained oxygen uptake and release is desired, minimal structuring of the microencapsulated spheres is preferred. Depending upon the physiological effect to be achieved, differing proportions of microencapsulated spheres of differing degrees of shell hardness can be combined. This will result in special release effects which can be used when introducing drugs, nutrients, enzyme systems. In other words, the composition can be so prepared as to give the desired specific rate of release of any of the components contained within the microencapsulated spheres. The procedure to incorporate drugs, nutrients, enzyme systems, et cetera, into synthetic blood containing microencapsulated stroma free hemoglobin is the same as the procedure herein described to incorporate drugs, nutrients, enzyme systems, et cetera, into synthetic blood containing microencapsulated hemoglobin.

CONCLUSION

A synthetic whole blood useful as a substitute for natural whole blood and a composition useful as a substitute for hematocrit and disclosed as are the methods of making these compositions. The synthetic whole blood is comprised of a two phase coacervate system with physicochemical and physiological properties that are very similar to those of whole natural blood. The hematocrit substitute is comprised of the coacervate phase of the two phase coacervate system.

In manufacturing the synthetic whole blood, ingredients such as electrolytes, stroma free hemoglobin, synthetic liposomes containing stroma free hemoglobin, microencapsulated stroma free hemoglobin, microspheres of albumin containing stroma free hemoglobin, or emulsified droplets made with the coacverate phase and containing stroma free hemoglobin, or an appropriate sterol can be incorporated. If desired, the synthetic whole blood can be used to introduce enzymes, nutriments and drug dosage forms into the recipient's circulation.

Animal experiments have demonstrated that this invention can be used as a substitute for natural whole blood and further, that the coacervate phase of the disclosed coacervate systems can be safely and effectively used as a substitute for hematocrit.

What is claimed is:

1. A method of preparing a synthetic whole blood substitute comprising the steps of:
   (A) dispersing an amount of albumin in a solution comprised of distilled water, about 0.9% weight to volume of a salt, from about 1% to about 5% weight to volume of urea and from about 0.1% to about 10% weight to volume of a phospholipid, as will result in about 5 to 25% weight to volume albumin in the final solution,
   (B) adding a non-polar solvent to the solution until globules of a coacervate phase of an aqueous two phase system begin to appear,
   (C) storing the solution, undisturbed at a temperature of from about 4° to 10° C., for at least 12 hours, thereby producing the two phase coacervate system, comprising an aqueous coacervate phase and an equilibrium bulk water phase,
   (D) removing said coacervate system from storage, allowing it to reach room temperature, then adding an amount of distilled water as will result in about 5 to 25% weight to volume of albumin, and
   (E) adding a sufficient amount of a salt to said coacervate system as will render it isotonic with whole human blood.

2. The method of claim 1 wherein the non polar solvent in (B) is glycerol dioleate, and the salt in (A) and (E) is NaCl.

3. A composition of matter useful as a substitute for whole blood which is prepared according to the method of claim 1.

4. The method of claim 1 wherein the two phases of the coacervate system are separated.

5. A composition of matter useful as a hematocrit substitute comprised of the coacervate phase prepared according to the method of claim 4.

6. The method of claim 1 which comprises the additional step of adding such amount of a sterol as will result in a 0.1 to 2% weight to volume concentration of the sterol in the coacervate system.